(12) United States Patent
Addison et al.

(10) Patent No.: US 12,329,436 B2  
(45) Date of Patent: Jun. 17, 2025

(54) CAUTERIZATION DEVICE FOR SEALING PLEURAL LAYERS

(71) Applicant: Bard Peripheral Vascular, Inc., Franklin Lakes, NJ (US)

(72) Inventors: Jordan Addison, Gilbert, AZ (US); Oladipo Peter Akerele-Ale, Phoenix, AZ (US); Eric Moll, Gilbert, AZ (US); Alexander Palmer, Scottsdale, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 454 days.

(21) Appl. No.: 17/781,200

(22) PCT Filed: Dec. 3, 2019

(86) PCT No.: PCT/US2019/064240  
§ 371 (c)(1),  
(2) Date: May 31, 2022

(87) PCT Pub. No.: WO2021/112828  
PCT Pub. Date: Jun. 10, 2021

(65) Prior Publication Data  
US 2023/0013276 A1   Jan. 19, 2023

(51) Int. Cl.  
*A61B 18/00* (2006.01)  
*A61B 18/08* (2006.01)

(52) U.S. Cl.  
CPC .. *A61B 18/082* (2013.01); *A61B 2018/00101* (2013.01); *A61B 2018/00541* (2013.01);  
(Continued)

(58) Field of Classification Search  
None  
See application file for complete search history.

(56) References Cited

U.S. PATENT DOCUMENTS 4,487,253 A * 12/1984 Malek ................... F28D 9/0006  
374/165  
4,966,597 A * 10/1990 Cosman ............. A61B 18/1492  
606/50  
(Continued)

FOREIGN PATENT DOCUMENTS

WO     0128488 A1    4/2001  
WO  2011037235 A1    3/2011

OTHER PUBLICATIONS

International Search Report and Written Opinion dated Jul. 20, 2020, in International Application No. PCT/US2019/064240.

*Primary Examiner* — Linda C Dvorak  
*Assistant Examiner* — Nicholas S Borsch  
(74) *Attorney, Agent, or Firm* — Dinsmore & Shohl LLP

(57) ABSTRACT

A cauterization device includes a handpiece configured to be grasped by a user. The handpiece includes a housing, a heat control circuit, and a control switch. A cannula has a cannula lumen, a cannula side wall surrounding the cannula lumen, a cannula proximal end portion, and a cannula distal end. The cannula proximal end portion is coupled to the housing of the handpiece. A stylet has a shaft portion and a distal heat conductive body. The distal heat conductive body is electrically coupled to the heat control circuit. The distal heat conductive body has a first end and a tapered portion that distally terminates at a second end. The shaft portion is located, at least in part, in the cannula lumen. The insulator member is configured to thermally separate the cannula distal end from the distal heat conductive body of the stylet.

18 Claims, 2 Drawing Sheets

(52) U.S. Cl.
CPC .............. *A61B 2018/00595* (2013.01); *A61B 2018/0072* (2013.01); *A61B 2018/00821* (2013.01)

(56) References Cited

U.S. PATENT DOCUMENTS

| | | | |
|---|---|---|---|
| 5,611,798 A * | 3/1997 | Eggers | A61B 18/10 219/241 |
| 6,592,530 B1 | 4/2003 | Farhadi | |
| 6,770,070 B1 | 8/2004 | Balbierz | |
| 6,981,949 B2 | 1/2006 | Hibner et al. | |
| 7,322,939 B2 | 1/2008 | Burbank et al. | |
| 7,422,563 B2 | 9/2008 | Roschak et al. | |
| 7,766,891 B2 | 8/2010 | Mcgurk et al. | |
| 8,147,483 B2 | 4/2012 | Tan | |
| 8,491,579 B2 | 7/2013 | Rossetto | |
| 8,568,404 B2 | 10/2013 | Brannan | |
| 8,709,034 B2 | 4/2014 | Keast et al. | |
| 8,958,887 B2 | 2/2015 | Hancock | |
| 8,992,413 B2 | 3/2015 | Bonn et al. | |
| 9,044,253 B2 | 6/2015 | Brannan | |
| 9,113,930 B2 | 8/2015 | Reid, Jr. | |
| 9,125,639 B2 | 9/2015 | Mathis et al. | |
| 9,247,993 B2 | 2/2016 | Ladtkow et al. | |
| 9,861,440 B2 | 1/2018 | Van Der Weide et al. | |
| 10,278,766 B2 | 5/2019 | Danek et al. | |
| 10,321,952 B2 | 6/2019 | Devries et al. | |
| 2003/0093007 A1 | 5/2003 | Wood | |
| 2003/0097079 A1 | 5/2003 | Garcia | |
| 2003/0109802 A1 | 6/2003 | Laeseke et al. | |
| 2005/0228312 A1 | 10/2005 | Surti | |
| 2005/0283147 A1* | 12/2005 | Yachi | A61B 18/082 606/28 |
| 2007/0073282 A1 | 3/2007 | Mcgaffigan et al. | |
| 2014/0128860 A1 | 5/2014 | Hosaka et al. | |
| 2017/0014187 A1* | 1/2017 | Wang | A61B 18/28 |
| 2017/0128126 A1 | 5/2017 | Sunenshine et al. | |
| 2017/0252091 A1* | 9/2017 | Honda | A61B 18/1445 |
| 2018/0296197 A1 | 10/2018 | Kronstrm et al. | |
| 2019/0076164 A1 | 3/2019 | Boyle, Jr. et al. | |
| 2019/0099219 A1 | 4/2019 | Thomas et al. | |
| 2019/0167407 A1 | 6/2019 | Schaer et al. | |

* cited by examiner

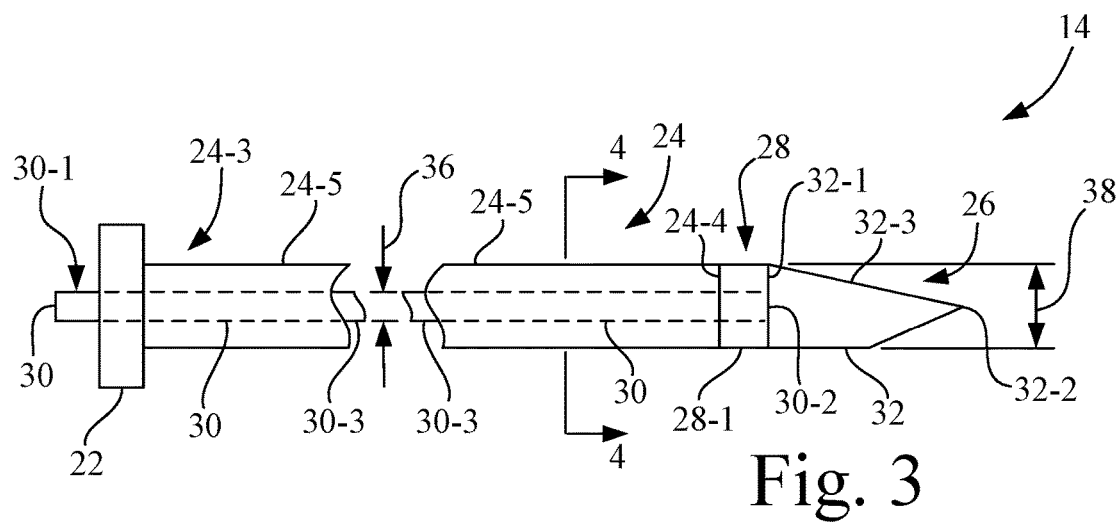
Fig. 3
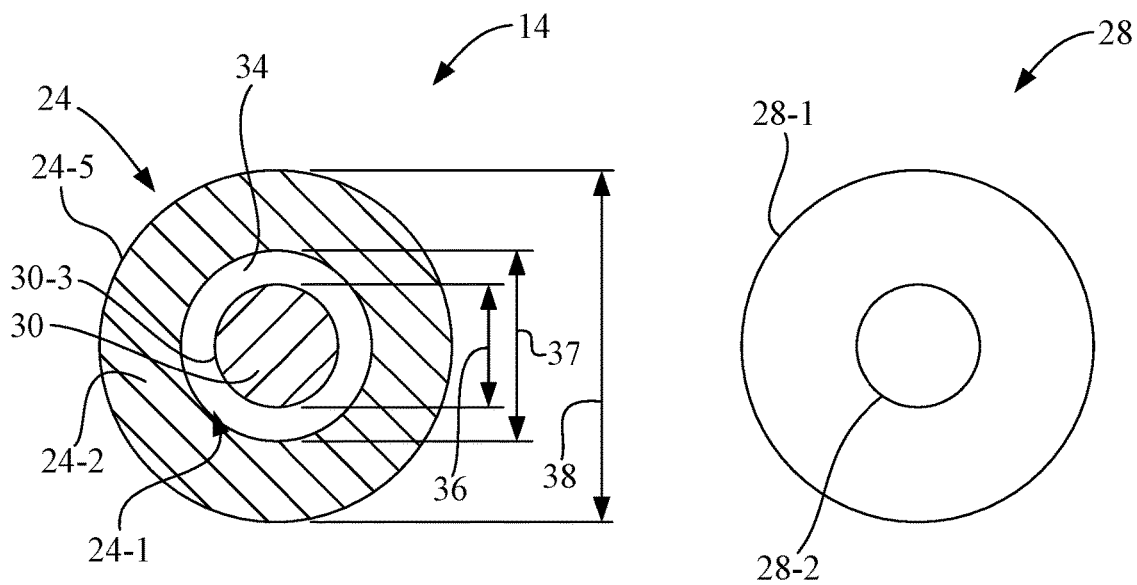
Fig. 4
Fig. 6
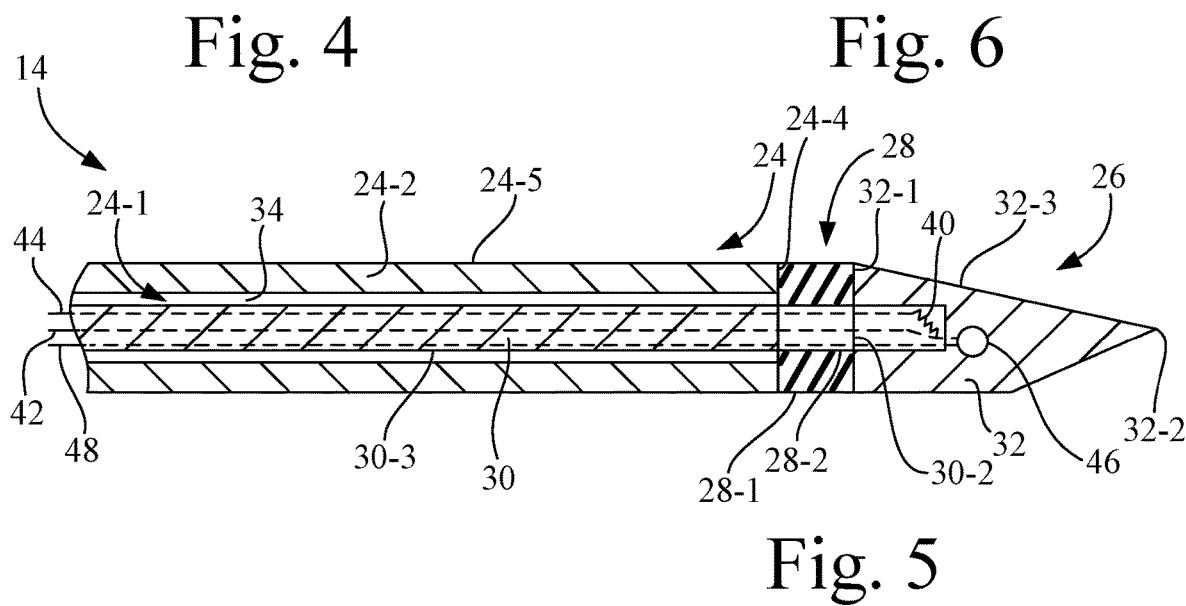
Fig. 5

CAUTERIZATION DEVICE FOR SEALING PLEURAL LAYERS

CROSS-REFERENCE TO RELATED APPLICATIONS

This application is a U.S. National Phase of International Application No. PCT/US2019/064240, entitled "CAUTERIZATION DEVICE FOR SEALING PLEURAL LAYERS" and filed Dec. 3, 2019, which is incorporated herein by reference in its entirety.

TECHNICAL FIELD

The present invention relates to devices used to facilitate lung access procedures, and, more particularly, to a cauterization device for sealing pleural layers.

BACKGROUND ART

Pneumothorax is a problematic complication of the lung biopsy procedure where air or fluid is allowed to pass into the pleural space as a result of the puncture of the parietal pleura and visceral pleura. Pneumothorax and, more so, pneumothorax requiring chest tube placement, are significant concerns for clinicians performing, and patients undergoing, percutaneous lung biopsies. The incidence of pneumothorax in patients undergoing percutaneous lung biopsy has been reported to be anywhere from 9-54%, with an average of around 15%. On average, 6.6% of all percutaneous lung biopsies result in pneumothorax requiring a chest tube to be placed, which results in an average hospital stay of 2.7 days.

Factors that increase the risk of pneumothorax include increased patient age, obstructive lung disease, increased depth of a lesion, multiple pleural passes, increased time that an access needle lies across the pleura, and traversal of a fissure. Pneumothorax may occur during or immediately after the procedure, which is why typically a CT scan of the region is performed following removal of the needle. Other, less common, complications of percutaneous lung biopsy include hemoptysis (coughing up blood), hemothorax (a type of pleural effusion in which blood accumulates in the pleural cavity), infection, and air embolism.

What is needed in the art is a cauterization device for sealing pleural layers.

SUMMARY OF INVENTION

The present invention provides a cauterization device for sealing pleural layers to aid in reducing the occurrence of pneumothorax associated with a lung access procedure.

The invention, in one form, is directed to a cauterization device that includes a handpiece, a cannula, and a stylet. The handpiece is configured to be grasped by a user. The handpiece includes a housing, a heat control circuit, and a control switch. The control switch is configured to selectively actuate the heat control circuit. A cannula has a cannula lumen, a cannula side wall surrounding the cannula lumen, a cannula proximal end portion, and a cannula distal end. The cannula proximal end portion is coupled to the housing of the handpiece. A stylet has a shaft portion and a distal heat conductive body. The distal heat conductive body is electrically coupled to the heat control circuit. The distal heat conductive body has a first end and a second end, and has a tapered portion that distally terminates at the second end. The shaft portion is located, at least in part, in the cannula lumen without contacting the cannula side wall. An insulator member is configured to thermally separate the cannula distal end from the distal heat conductive body of the stylet.

The invention, in another form, is directed to an electrocautery probe that includes a hub, a cannula, a stylet, and an insulator member. The cannula has a cannula lumen, a cannula side wall surrounding the cannula lumen, a cannula proximal end portion, and a cannula distal end. The cannula proximal end portion is coupled to the hub. The stylet has a shaft portion and a distal heat conductive body. The shaft portion is coupled to the hub. The distal heat conductive body has a first end and a second end, and has a tapered portion that distally terminates at the second end. The shaft portion is located, at least in part, in the cannula lumen without contacting the cannula side wall. An insulator member is interposed between, and attached to, the cannula distal end and the first end of the distal heat conductive body of the stylet. The insulator member is configured to thermally separate the cannula distal end from the distal heat conductive body of the stylet.

An advantage of the present invention is that construction of the cauterization device reduces the chance of patient injury associated with unintentional heating along an insertion/access tract.

Another advantage is that, in a lung access procedure, the distal heat conductive body of the stylet of the electrocautery probe is effective to induce pleurodesis, wherein the pleural space is artificially obliterated via the adhesion of the two pleural layers by the thermal effects produced by the distal heat conductive body engaging the pleural layers at a cauterization temperature, thereby reducing or eliminating the risk of pneumothorax during the lung access procedure, such as a lung biopsy.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 3 is an enlarged side view of the electrocautery probe of FIG. 1, with a section broken away;

FIG. 4 is a further enlarged section view of the electrocautery probe taken along line 4-4 of FIG. 3;

FIG. 5 is an enlarged section view of a distal portion of the electrocautery probe taken along plane 5-5-5-5 of FIG. 1, and showing a heating element and a thermocouple in schematic form; and FIG. 6 is an enlarged end view of the insulator member of the electrocautery probe depicted in FIGS. 1, 3, and 5.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
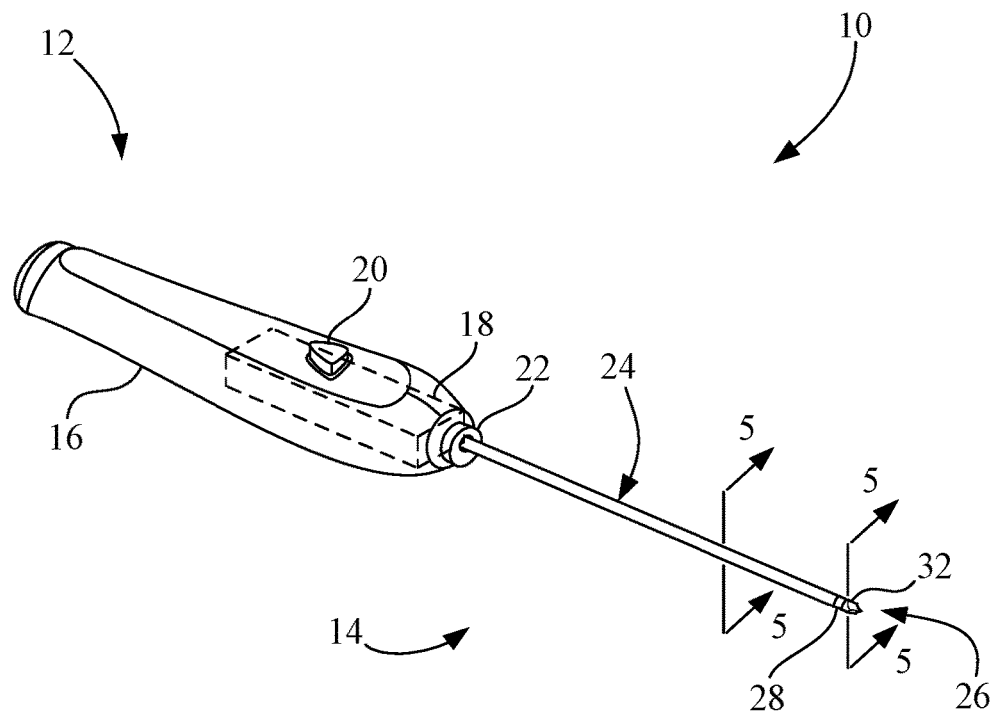
FIG. 1 is a perspective view of a cauterization device including an electrocautery probe, in accordance with an aspect of the present invention.

Referring now to the drawings, and more particularly to FIG. 1, there is shown a cauterization device 10 which generally includes a handpiece 12 and an electrocautery probe 14.

Handpiece 12 is configured, e.g., sized and shaped, to be grasped by a user. Handpiece 12 is mechanically coupled to the electrocautery probe 14. In one embodiment, for example, electrocautery probe 14 may be removably coupled to handpiece 12, such that handpiece 12 may be reusable, while electrocautery probe 14 may be disposable. As used herein, the term disposable means intended for use on a single patient and is discarded in an environmentally safe manner after that use. Alternatively, electrocautery probe 14 may be permanently coupled to handpiece 12, such that handpiece 12 and electrocautery probe 14 may be disposable as a unit after use.

Figure 2:
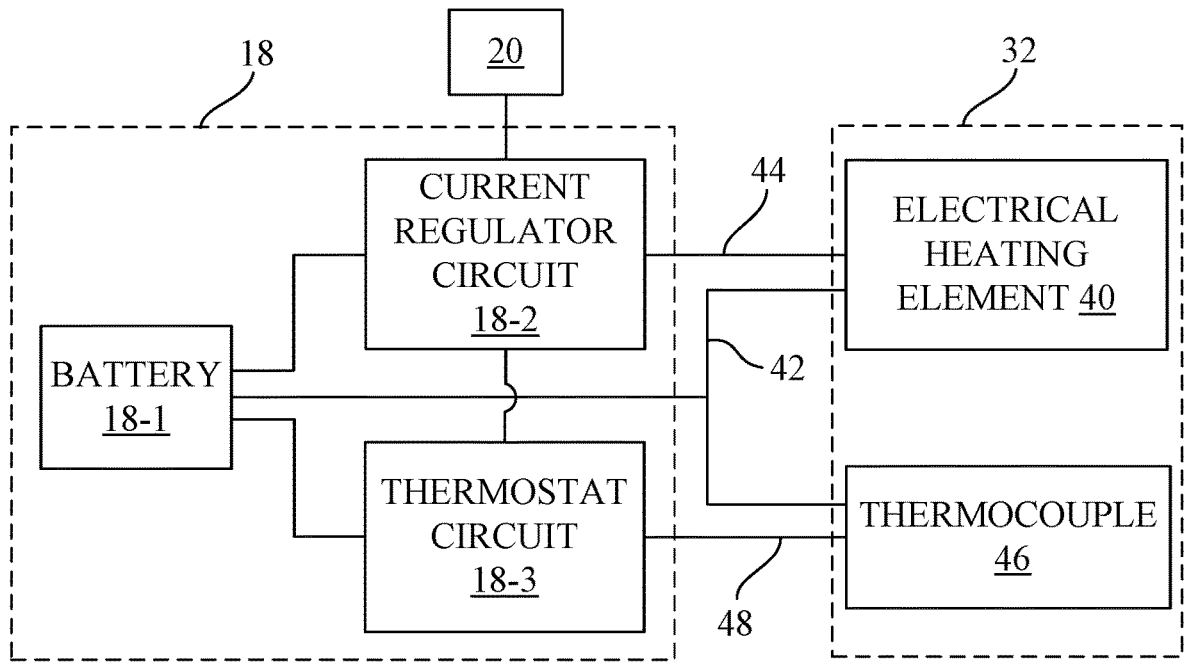
FIG. 2 is an electrical block diagram of a heat control circuit and a distal heat conductive body of the cauterization device of FIG. 1.

Referring also to FIG. 2, handpiece 12 includes a housing 16, a heat control circuit 18, and a control switch 20. Control switch 20 may be, for example, a push button switch that is configured to selectively actuate, e.g., turn ON and OFF, heat control circuit 18. Heat control circuit 18 may be, for example, a DC or AC power source that may include a battery 18-1 and a current regulator circuit 18-2, and may optionally include a thermostat circuit 18-3. Heat control circuit 18 is electrically coupled to electrocautery probe 14 to supply electrical current via current regulator circuit 18-2 to electrocautery probe 14 to cause electrical, e.g., resistive, heating of a heating component of electrocautery probe 14, as will be described in more detail below.

Optionally, it is contemplated that heat control circuit 18 may be adjusted to control heating time, maximum temperature, and overall lifetime of electrocautery probe 14. Also, heat control circuit 18 may include capacitors to store current and allow battery 18-1 to operate at a lower current and fit into a smaller footprint while still producing the same amount of heating current, and thereby heat, over a short time period. A capacitor may also be used to get the heating component of electrocautery probe 14 hotter quicker by providing a current burst at the onset of heating electrocautery probe 14.

Referring also to FIG. 3, electrocautery probe 14 includes a hub 22, cannula 24, a stylet 26, and an insulator member 28.

Hub 22 serves as a connector base for cannula 24 and stylet 26, and is configured to be coupled, e.g., by a bayonet-type mount, to housing 16 of handpiece 12, wherein hub 22 is removably connected to the handpiece 12. Alternatively, hub 22 may be permanently connected to handpiece 12. To avoid heat transfer from stylet 26 to cannula 24, hub 22 is thermally insulated from at least one of cannula 24 and the stylet 26. In the present embodiment, hub 22 may be made from a thermal insulating material, such as for example, a heat-resistant plastic (e.g., a non-melting or thermal deforming polymer) or ceramic.

Referring to FIGS. 3-5, cannula 24 includes a cannula lumen 24-1, a cannula side wall 24-2, a cannula proximal end portion 24-3, a cannula distal end 24-4, and a cannula outer surface 24-5. Cannula proximal end portion 24-3 is coupled to the hub 22, e.g., connected by an adhesive or press-fit attachment, and thus, is coupled to housing 16 of handpiece 12 via hub 22. Cannula side wall 24-2 surrounds cannula lumen 24-1. Cannula 24 may be made from a biocompatible material, such as for example, a biocompatible metal (e.g., stainless steel, nitinol, titanium, etc.). Optionally, cannula 24 may be made from the biocompatible metal having a thermal insulating coating or tubular covering, such as a ceramic coating that forms cannula outer surface 24-5 of cannula 24. As a further alternative, it is contemplated that cannula 24 may be formed from a thermal insulating material, such as plastic or ceramic.

Referring to FIG. 3-5, stylet 26 includes a shaft portion 30, and a distal heat conductive body 32. In the present embodiment, shaft portion 30 and distal heat conductive body 32 of stylet 26 are formed as a unitary structure, which may be a single piece construction or a multi-piece construction. Stylet 26 may be made from a biocompatible metal (e.g., stainless steel, nitinol, titanium, etc.). Shaft portion 30 is coupled to hub 22, e.g., connected by an adhesive or press-fit attachment, and thus, is coupled to housing 16 of handpiece 12 via hub 22. Shaft portion 30 includes a shaft proximal portion 30-1, a shaft distal end 30-2, and a shaft outer surface 30-3. As shown in FIG. 3, at least part of shaft proximal portion 30-1 of shaft portion 30 may extend proximally from hub 22 to serve as a mechanical cantilever mounting support when electrocautery probe 14 is attached to handpiece 12 of cauterization device 10, and/or to facilitate electrical connections with heat control circuit 18 in handpiece 12.

In the present embodiment, with reference to FIGS. 4 and 5, shaft portion 30 is located, at least in part, in cannula lumen 24-1, and without any portion of shaft portion 30 contacting cannula side wall 24-2. More particularly, a cylindrical void 34 in cannula lumen 24-1 separates cannula side wall 24-2 of cannula 24 from shaft portion 30 of stylet 26. Cylindrical void 34 may be filled with air and/or a thermal insulating material (e.g., a heat-resistant plastic or ceramic). To form cylindrical void 34, shaft portion 30 of stylet 26 has a first diameter 36 that is smaller than an inner diameter 37 of cannula lumen 24-1 of cannula 24 (see, e.g., FIG. 4).

As best shown in FIGS. 3 and 5, distal heat conductive body 32 of stylet 26 has a first end 32-1, second end 32-2, and having a tapered portion 32-3 that distally terminates at second end 32-2, with second end 32-2 forming a penetrating tip. In addition, distal heat conductive body 32 has a second diameter 38 at first end 32-1 that is larger than the first diameter 36 of shaft portion 30, and with second diameter 38 at first end 32-1 of distal heat conductive body 32 of stylet 26 corresponding generally in size to the outer diameter of cannula 24.

Referring again to FIG. 2, distal heat conductive body 32 of stylet 26 is electrically coupled to heat control circuit 18. Referring again also to FIG. 5, in the present embodiment, an electrical heating element 40 is attached to, e.g., embedded in, distal heat conductive body 32 of stylet 26, which in turn is electrically coupled to heat control circuit 18. Electrical heating element 40 may be in the form of a resistive heating device, such as an electrical filament, or other such electrically resistive component that generates heat when energized with electrical current. Potential filament materials include, for example, tungsten, bismuth, aluminum, tin, iron, stainless steel, or alloys from two or more of the above materials.

A pair of electrodes 42, 44 extends through electrocautery probe 14, from hub 22 and through the cannula lumen 24-1 to distal heat conductive body 32 of stylet 26. The pair of electrodes 42, 44 is proximally electrically connected to the power source, e.g., battery 18-1 and current regulator circuit 18-2, of heat control circuit 18, and is distally electrically connected to electrical heating element 40 in distal heat conductive body 32 of stylet 26. Thus, heat control circuit 18 is electrically coupled to electrocautery probe 14 to supply electrical current via current regulator circuit 18-2 to electrical heating element 40 of distal heat conductive body 32 of stylet 26 of electrocautery probe 14, so as to cause electrical, e.g., resistive, heating of electrical heating element 40 of distal heat conductive body 32 of stylet 26 of electrocautery probe 14.

In the present embodiment, the pair of electrodes 42, 44 is thermally and electrically insulated from cannula side wall 24-2 of cannula 24 and stylet 26. The pair of electrodes 42, 44 may be mechanically coupled to one of an inner surface of the cannula side wall 24-2, or alternatively, may be mechanically coupled to stylet 26, e.g., an outer surface of shaft portion 30 of stylet 26. Such mechanical coupling may be, for example, in the form of embedding in cannula side wall 24-2 or stylet 26. Alternatively, an elongate trough may be formed in cannula side wall 24-2 and/or shaft portion 30 of stylet 26 to carry a respective electrode of the pair of electrodes 42, 44 for connection to electrical heating element 40 of distal heat conductive body 32 of stylet 26, wherein the pair of electrodes 42, 44 may be restrained in the trough(s) via an adhesive/encapsulant.

As a further alternative, it is contemplated that stylet 26, in metal form, may serve as a common electrode, e.g., electrode 42, of the pair of electrodes 42, 44, with the pair of electrodes 42, 44 being connected to electrical heating element 40 of distal heat conductive body 32 of stylet 26.

Optionally, a thermocouple 46 may be attached to, e.g., embedded in, distal heat conductive body 32 of stylet 26. In such an embodiment, thermocouple 46 is electrically coupled to the optional thermostat circuit 18-3 of heat control circuit 18, e.g., by the common electrode 42 and a thermocouple electrode 48. Thus, thermocouple 46 monitors the temperature of distal heat conductive body 32 of the stylet 26, and supplies temperature signals to thermostat circuit 18-3 via electrodes 42, 48, so as to maintain a power output of current regulator circuit 18-2 in a desired range to in turn maintain the temperature of distal heat conductive body 32 of the stylet 26 in a safe and effective operating temperature range. For example, heat control circuit 18 may be configured to maintain a temperature of distal heat conductive body 32 of the stylet 26, as determined by temperature readings received from thermocouple 46, in a range of 70 degrees Celsius (C) to 120 degrees C.

Referring to FIGS. 5 and 6, insulator member 28 is interposed between, and is attached to (e.g., by an adhesive or an interference fit) each of cannula distal end 24-4 of cannula 24 and first end 32-1 of distal heat conductive body 32 of stylet 26. Insulator member 28 is configured to thermally separate cannula distal end 24-4 from distal heat conductive body 32 of stylet 26. Insulator member 28 is made from a thermal insulating material, such as for example, a heat-resistant plastic (e.g., a non-melting or thermal deforming polymer) or a ceramic.

In the present embodiment, insulator member 28 is configured as an annular body 28-1 that defines an opening 28-2, wherein shaft portion 30 of the stylet 26 is configured to be received through opening 28-2 of annular body 28-1 of insulator member 28. Also, the electrodes 42, 44, 48 that provide electrical connection to the electrical components of distal heat conductive body 32 of stylet 26 are received through opening 28-2 of annular body 28-1 of insulator member 28. A thickness of insulator member 28 defines a longitudinal separation distance between first end 32-1 of distal heat conductive body 32 of the stylet 26 and cannula distal end 24-4 of cannula 24.

During a lung access procedure, for example, distal heat conductive body 32 of stylet 26 of electrocautery probe 14 is inserted into the chest cavity of a patient along an access tract, and second end 32-2 that forms the piercing tip of distal heat conductive body 32 is brought near the location of the pleural layers. The user then actuates control switch 20, which in turn actuates heat control circuit 18, so as to generate heating of distal heat conductive body 32 of stylet 26 of electrocautery probe 14 in a range of 70 degrees C. to 120 degrees C. As the distal heat conductive body 32 is further advanced into and through the pleural layers, pleurodesis is induced, wherein the pleural space is artificially obliterated via the adhesion of the two pleural layers by the thermal effects produced by distal heat conductive body 32 engaging the pleural layers at a cauterization temperature. As a result, the risk for pneumothorax during a lung access procedure, e.g., a biopsy procedure, utilizing the access tract is reduced or eliminated.

The following items also relate to the invention:

In one form, the invention relates to a cauterization device that may include a handpiece, a cannula, a stylet and an insulator member, i.e. a handpiece and an electrocautery probe. The handpiece may be configured to be grasped by a user. The handpiece includes a housing, a heat control circuit, and a control switch. The control switch may be configured to selectively actuate the heat control circuit. The cannula may have a cannula lumen, a cannula side wall surrounding the cannula lumen, a cannula proximal end portion, and a cannula distal end. The cannula proximal end portion may be coupled to the housing of the handpiece. The stylet may have a shaft portion and a distal heat conductive body. The distal heat conductive body may be electrically coupled to the heat control circuit. The distal heat conductive body has a first end and a second end, and has a tapered portion that distally terminates at the second end. The shaft portion may be located, at least in part, in the cannula lumen without (directly) contacting the cannula side wall. The insulator member is configured and arranged in the cauterization device so as to thermally separate the cannula distal end from the distal heat conductive body of the stylet.

In some embodiments, the insulator member may be interposed between, and attached to, the cannula distal end and the first end of the distal heat conductive body of the stylet.

In some embodiments, the shaft portion may have a first diameter and the distal heat conductive body has a second diameter larger than the first diameter.

In some embodiments, an electrical heating element may be embedded in the distal heat conductive body of the stylet. A pair of electrodes may extend through the cannula lumen. The pair of electrodes may be configured to be thermally and electrically insulated from the cannula side wall. The pair of electrodes may be connected to each of the heat control circuit and the electrical heating element in the distal heat conductive body of the stylet.

In the embodiment of the immediately preceding paragraph, the pair of electrodes may be mechanically coupled to one of an inner surface of the cannula side wall or an outer surface of the shaft portion of the stylet.

In some embodiments, the insulator member optionally may be configured as an annular body that defines an opening, wherein the shaft portion of the stylet may be configured to be received through the opening of the annular body.

In some embodiments, the insulator member may be made from at least one of a heat-resistant plastic and a ceramic.

In some embodiments, the cauterization device comprises a cylindrical void in the cannula lumen, which void separates the cannula side wall from the shaft portion of the stylet.

In some embodiments, the cylindrical void may be filled with at least one of an insulating material and air.

In some embodiments, the cannula and the stylet may be configured as an electrocautery probe, and the cauterization device/electrocautery probe may further comprise a hub connected to each of the cannula proximal end portion and the shaft portion of the stylet, wherein the hub may be removably connected to the handpiece.

In some embodiments, optionally, a thermocouple may be attached to the distal heat conductive body of the stylet, wherein the thermocouple may be electrically coupled to the heat control circuit.

In some embodiments, the heat control circuit may be configured to maintain a temperature of the distal heat conductive body of the stylet in a range of 70 degrees Celsius (C) to 120 degrees C.

In another form, the invention relates to an electrocautery probe that may include a hub, a cannula, a stylet, and an insulator member. The cannula may have a cannula lumen, a cannula side wall surrounding the cannula lumen, a cannula proximal end portion, and a cannula distal end. The cannula proximal end portion may be coupled to the hub. The stylet may have a shaft portion and a distal heat conductive body. The shaft portion may be coupled to the hub. The distal heat conductive body has a first end and a second end, and has a tapered portion that distally terminates at the second end. The shaft portion may be located, at least in part, in the cannula lumen without contacting the cannula side wall. The insulator member may be interposed between, and attached to, the cannula distal end and the first end of the distal heat conductive body of the stylet. The insulator member is configured and arranged in the electrocautery probe so as to thermally separate the cannula distal end from the distal heat conductive body of the stylet.

In some embodiments, the shaft portion has a first diameter and the distal heat conductive body has a second diameter larger than the first diameter.

In some embodiments, an electrical heating element may be embedded in the distal heat conductive body of the stylet. A pair of electrodes may extend from the hub and through the cannula lumen. The pair of electrodes may be configured to be thermally and electrically insulated from the cannula side wall. The pair of electrodes may be connected to the electrical heating element in the distal heat conductive body of the stylet.

In the embodiment of the immediately preceding paragraph, the pair of electrodes may be mechanically coupled to one of an inner surface of the cannula side wall or an outer surface of the shaft portion of the stylet.

In some embodiments, the insulator member may be configured as an annular body that defines an opening, wherein the shaft portion of the stylet may be configured to be received through the opening of the annular body.

In some embodiments, the insulator member may be made from at least one of a heat-resistant plastic and a ceramic.

In some embodiments, the electrocautery probe comprises a cylindrical void in the cannula lumen, which void separates the cannula side wall from the shaft portion of the stylet, and wherein the cylindrical void optionally may be at least partially filled with one of air and an insulating material.

In some embodiments, the hub may be thermally insulated from at least one of the cannula and the stylet.

As used herein, words of degree, such as "generally", are relative modifiers intended to indicate permissible variation from the characteristic so modified. It is not intended to be limited to the absolute value or characteristic which it modifies but rather possessing more of the physical or functional characteristic than its opposite, and approaching or approximating such a physical or functional characteristic.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A cauterization device, comprising:
   a handpiece configured to be grasped by a user, the handpiece including a housing, a heat control circuit, and a control switch, the control switch configured to selectively actuate the heat control circuit;
   a cannula having a cannula lumen, a cannula side wall surrounding the cannula lumen, a cannula proximal end portion, and a cannula distal end, the cannula proximal end portion being coupled to the housing of the handpiece;
   a stylet having a shaft portion and a distal heat conductive body, the shaft portion and the distal heat conductive body together are formed as a unitary structure of a single piece construction, wherein the stylet is made of a biocompatible metal, the distal heat conductive body being electrically coupled to the heat control circuit, the distal heat conductive body having a first end and a second end, and having a tapered portion that distally terminates at the second end, the shaft portion being at least partially located in, and extending through, the cannula lumen without contacting the cannula side wall to provide a cantilevered support for the distal heat conductive body; and
   an insulator member having an annular body that defines an opening that receives the shaft portion of the stylet, the insulator member positioned between the cannula distal end and the distal heat conductive body to thermally separate the cannula distal end from the distal heat conductive body of the stylet.

2. The cauterization device according to claim 1, wherein the insulator member is interposed between, and attached to, the cannula distal end and the first end of the distal heat conductive body of the stylet.

3. The cauterization device according to claim 1, wherein the shaft portion has a first diameter and the distal heat conductive body has a second diameter larger than the first diameter.

4. The cauterization device according to claim 1, further comprising:
   an electrical heating element embedded in the distal heat conductive body of the stylet; and
   a pair of electrodes that extend through the cannula lumen, the pair of electrodes being thermally and electrically insulated from the cannula side wall, the pair of electrodes being connected to each of the heat control circuit and the electrical heating element in the distal heat conductive body of the stylet.

5. The cauterization device according to claim 4, wherein the pair of electrodes is mechanically coupled to one of an inner surface of the cannula side wall or an outer surface of the shaft portion of the stylet.

6. The cauterization device according to claim 1, wherein the insulator member is made from at least one of a heat-resistant plastic and a ceramic.

7. The cauterization device according to claim 1, wherein a cylindrical void in the cannula lumen separates the cannula side wall from the shaft portion of the stylet.

8. The cauterization device according to claim 7, wherein the cylindrical void is filled with at least one of an insulating material and air.

9. The cauterization device according to claim 1, wherein the cannula and the stylet are configured as an electrocautery probe, further comprising a hub connected to each of the cannula proximal end portion and the shaft portion of the stylet, wherein the hub is removably connected to the handpiece.

10. The cauterization device according to claim 1, further comprising a thermocouple attached to the distal heat conductive body of the stylet, the thermocouple being electrically coupled to the heat control circuit.

11. The cauterization device according to claim 1, wherein the heat control circuit is configured to maintain a temperature of the distal heat conductive body of the stylet in a range of 70 degrees Celsius (C) to 120 degrees C.

12. An electrocautery probe, comprising:
a hub;
a cannula having a cannula lumen, a cannula side wall surrounding the cannula lumen, a cannula proximal end portion, and a cannula distal end, the cannula proximal end portion being coupled to the hub;
a stylet having a shaft portion and a distal heat conductive body, the shaft portion and the distal heat conductive body together are formed as a unitary structure of a single piece construction, wherein the stylet is made of a biocompatible metal, the shaft portion being coupled to the hub to provide a cantilevered support for the distal heat conductive body, the distal heat conductive body having a first end and a second end, and having a tapered portion that distally terminates at the second end, the shaft portion being located, at least in part, in the cannula lumen without contacting the cannula side wall; and
an insulator member interposed between, and attached to, the cannula distal end and the first end of the distal heat conductive body of the stylet, the insulator member having an annular body that defines a bore through which the shaft portion of the stylet extends, the insulator member configured to thermally separate the cannula distal end from the distal heat conductive body of the stylet.

13. The electrocautery probe according to claim 12, wherein the shaft portion has a first diameter and the distal heat conductive body has a second diameter larger than the first diameter.

14. The electrocautery probe according to claim 12, further comprising:
an electrical heating element embedded in the distal heat conductive body of the stylet; and
a pair of electrodes that extend from the hub and through the cannula lumen, the pair of electrodes being thermally and electrically insulated from the cannula side wall, the pair of electrodes being connected to the electrical heating element in the distal heat conductive body of the stylet.

15. The electrocautery probe according to claim 14, wherein the pair of electrodes is mechanically coupled to one of an inner surface of the cannula side wall or an outer surface of the shaft portion of the stylet.

16. The electrocautery probe according to claim 12, wherein the insulator member is made from at least one of a heat-resistant plastic and a ceramic.

17. The electrocautery probe according to claim 12, wherein a cylindrical void in the cannula lumen separates the cannula side wall from the shaft portion of the stylet, and wherein the cylindrical void is at least partially filled with one of air and an insulating material.

18. The electrocautery probe according to claim 12, wherein the hub is thermally insulated from at least one of the cannula and the stylet.

* * * * *